United States Patent
Mucha et al.

(10) Patent No.: US 9,410,802 B2
(45) Date of Patent: Aug. 9, 2016

(54) METHOD FOR CHECKING POSITION DATA OF A MEDICAL INSTRUMENT, AND CORRESPONDING MEDICAL INSTRUMENT

(75) Inventors: Dirk Mucha, Berlin (DE); Timo Krueger, Berlin (DE)

(73) Assignee: FIAGON GMBH, Berlin (DE)

(*) Notice: Subject to any disclaimer, the term of this patent is extended or adjusted under 35 U.S.C. 154(b) by 848 days.

(21) Appl. No.: 13/810,666

(22) PCT Filed: Jul. 16, 2011

(86) PCT No.: PCT/EP2011/003563
§ 371 (c)(1),
(2), (4) Date: Apr. 18, 2013

(87) PCT Pub. No.: WO2012/007179
PCT Pub. Date: Jan. 19, 2012

(65) Prior Publication Data
US 2013/0211763 A1 Aug. 15, 2013

(30) Foreign Application Priority Data
Jul. 16, 2010 (DE) .......................... 10 2010 027 535

(51) Int. Cl.
*G01C 17/38* (2006.01)
*G01B 21/02* (2006.01)
*G01B 21/04* (2006.01)
*G01D 18/00* (2006.01)

(52) U.S. Cl.
CPC .............. *G01B 21/02* (2013.01); *G01B 21/045* (2013.01); *G01D 18/00* (2013.01); *A61B 2034/2072* (2016.02)

(58) Field of Classification Search
CPC ........ A61B 5/06; A61B 8/12; A61B 19/5244; A61B 2019/461; A61B 19/5225
USPC ......... 702/85, 94, 95, 104; 600/117, 409, 424
See application file for complete search history.

(56) References Cited

U.S. PATENT DOCUMENTS

2007/0106114 A1* 5/2007 Sugimoto ................ A61B 1/31
600/117

* cited by examiner

*Primary Examiner* — An Do (57) ABSTRACT

A method for checking situation and position data of an instrument with at least a first section having at least a first sensor and at least a second sensor. The method encompasses the metrological determination of the situation or position, or its change, of the first sensor and the second sensor, determining a variable feature of the spatial reference between the situation or position of the first sensor and the situation or position of the second sensor at least at a first point in time, at a second point in time and at a third point in time. The method further encompasses determining, by means of a criterion, whether a difference of the variable feature between a first expression at a first point in time and a second expression at a second point in time still exists at a third point in time.

22 Claims, 6 Drawing Sheets

METHOD FOR CHECKING POSITION DATA OF A MEDICAL INSTRUMENT, AND CORRESPONDING MEDICAL INSTRUMENT

CROSS-REFERENCE TO RELATED APPLICATIONS

This application is filed under 35 U.S.C. 371 as a U.S. national phase application of PCT/EP2011/003563, having an international filing date of 16 Jul. 2011, which claims the benefit of German Patent Application No. 10 2010 027 535.2, having a filing date of 16 Jul. 2010, both of which are hereby incorporated by reference.

TECHNICAL FIELD

The present invention relates to a method for checking the orientation or situation data or position data of an instrument and to a corresponding apparatus. If relates further to a digital storage medium, a computer program product, and a computer program.

BACKGROUND

When working with an instrument in an area that is not visible, it may be important to determine and display the present orientation or position of the instrument. It is known in the art that it is possible to provide an instrument with electromagnetic position sensors, known as coil elements. A field generator arranged in the vicinity of the instrument generates an electromagnetic field which induces voltage within the coil elements or inductor of the instrument in accordance with the law of electromagnetic induction. The value or amplitude of the induced voltage or the electric currents in the coil elements may vary in accordance with the spatial orientation or situation and in accordance with the positioning of the sensors on the instrument. The electromagnetic situation sensors may also be so-called saturation core magnetometers which provide a signal that is proportional to the local field strength of the generated electromagnetic field.

A control unit interconnected with the field generator and the situation sensors may subsequently compute the position of the sensors and, thus, the position of the instrument from the measurement data from the field generator and the situation sensors. The position of the sensors may be displayed on, for example, a monitor.

Methods for determining the orientations or situations of instruments based on optical measurement principles using suitable sensors arranged on the instruments are also known.

Further, methods for failure detection are known for rigid instruments which do not deform during use. These methods for failure detection are based on the principle that two different sensors arranged on the instrument differently reference a certain area of the instrument at a point in time and hence determine different position data. That way, an erroneous measurement of at least one sensor is concluded. If such methods are used with instruments that deform during use the situation data of the deformed instrument may not unambiguously be distinguished from possible erroneous situation data. In particular, also due to the deformation of the instrument, situation data are considered to be erroneous, although there is no interference.

It is an object of the present invention to suggest a method that allows for detecting erroneously determined situation or position data of an instrument or their review.

SUMMARY

According to that method, the instrument comprises at least two different sections, a first one and a second one. The form or the function, or both, of the two sections may be the same or different from each other. The first section comprises at least a first sensor, the second section also comprises at least one sensor which is hereafter called the second sensor. The method comprises the metrological determination of the spatial situation or position of the first and the second sensor, or changes thereof.

Advantageous developments of the object according to the present invention are subject-matter of the sub-claims.

Based on the determination by of the criterion, in some embodiments according to the invention a distinction is made between whether the difference in the expression of the variable feature between the first expression at the first point in time ($t_1$) and the second expression at the second point in time ($t_2$) is based on a deformation or bending or deflection of the instrument or on a different impact on the measured spatial reference, such as, for example, an artifact or a interference.

The term "situation" (or "orientation") as used herein describes, in certain embodiments of the present invention, the situation of a sensor as a spatial position and the orientation of a three-dimensional geometric body.

The term situation may be used as a synonym for the term situation or orientation data. The situation data quantitatively describe the situation in a reference system.

The term "position" as used herein describes, in certain embodiments of the present invention, the spatial location or the existence of a three-dimensional geometric body.

The term position may be used as a synonym for the term position data. The position data quantitatively describe the position in a reference system.

In one step of the method according to the invention an expression of a variable feature of the spatial reference between the situation of the first sensor and the situation of the second sensor is determined at at least three points in time each, namely a first point in time, a second point in time and a third point in time.

In a further step, it is determined, by of a criterion, in particular a predetermined one, whether a difference between a first expression or amplitude of the variable feature at a first point in time and a second expression of the variable feature at a second point in time still exists at a third point in time.

Knowing the difference in expression or amplitude—which is determinable according to the present invention—of the variable feature between the first expression at the first point in time and the second expression at the second point in time on the one hand and, on the other hand, its continuance (of the respective expressions) at the third point in time by a criterion, may make it advantageously possible, in certain embodiments according to the present invention to identify a failure detection of situation data and/or detect an existing deformation of the instrument.

The determination of the relative situation or the situations of the first sensor and the second sensor to each other may take place computationally.

The term "relative to each other" as used herein describes the situation of the first sensor with reference to the second sensor. The situation of the second sensor with reference to the first sensor may be described equally.

The situation of a sensor may be displayed in a coordinate system by its coordinates.

The mathematical description of the situation of a sensor—which in the sense of the present invention may also be designated as locator or as situation sensor—may take place by a matrix representation using a coordinate system.

Matrices can be used for the computational or mathematical situation description of a first sensor with reference to the situation of a second sensor. The matrix of the first sensor (synonymous with: the matrix of the position of the first sensor, displayed or described by its matrix as spatial position description) may be transformed onto the matrix of the second sensor. The situation description of the first sensor with reference to the second sensor (or vice versa) is then described by a transformation matrix.

By the transformation matrix, the coordinates of the first sensor may be transformed onto the second sensor. Put differently, a coordinate transformation of the coordinates of the first sensor onto the coordinates of the second sensor is carried out.

A variable feature of the spatial reference may be a coordinate transformation or its result.

A variable feature may be a feature that is variable in time.

A feature that is variable in time may be contemplated at a first point in time $t_1$, at a second point in time $t_2$, at a third point in time $t_3$ and in addition at other points in time $t_i$ ($t_i$ for i=4, 5, 6, 7 . . . ).

In some embodiments according to the present invention, all considered points in time $t_i$ ($t_i$ for i=1, 2, 3, 4, 5, 6, 7 . . . )—in other embodiments according to the present invention only the points in time $t_1$, $t_2$ and $t_3$—each lie after the beginning of a treatment of the patient by the instrument.

In case of a deformation of the instrument, the expression of the variable feature (which then may be called or designated as permanent change or expression) of the spatial reference at a third point in time ($t_3$) may be set as new initial expression. At the point in time $t_3$ the deformed instrument may then be considered as initial expression for further points in time $t_i$ ($t_i$ for i=4, 5, 6, 7 . . . ).

The coordinate transformation from the first sensor to the second sensor can be described mathematically, as can the coordinate transformation from the second sensor to the first sensor. The coordinate transformation from the second sensor to the first section of the instrument is also possible, just as is the coordinate transformation from the first sensor to the second section. Furthermore, the coordinate transformation from the first sensor to the first section is possible, just as is the coordinate transformation from the second sensor to the second section.

The "first section" or the "second section," or a spot of the first or second section may be the tip of the instrument or a medically effective section hereof, for example a cutting surface or face. The first or second section may, alternatively, be any other section or encompass such.

Each of the provided sensors may be arranged on the surface of the instrument or within the instrument or the sections. It may for example be advantageous to encapsulate at least one sensor in the instrument if it is not to come into contact with the environment. This may either serve to protect the sensor from the ambient medium, but also vice versa; to protect the ambient medium or tissue from the sensor. Possible applications are measurements in toxic and/or aggressive substances that could destroy the sensor or applications in the vicinity of human or animal tissue that could be influenced by sensor materials.

The sensor may contain one or several coils or it may consist hereof.

The coil or the coils have in certain embodiments a continuous or reach-through or patent interior. This interior may have an arbitrary cross-section; it can for example be round, oval, rectangular or polygonal. The patency of the interior may be in a longitudinal direction of the coil. The continuity or patency of the interior may—in a state of use of the instrument the coil is connected with—exist in a longitudinal direction of the instrument or of a section that comprises the coil.

Patency or continuity is in certain embodiments according to the present invention to be understood as the possibility of leading or sliding, for example, a further instrument, (i.e. a different one to the the one the coil in its state of use is firmly connected with in the sense of the present invention), through the interior of the coil. Patency may in some embodiments according to the present invention be understood as the possibility of operating or acting through or along the coil.

The coil or the coils may be arranged around a section of the instrument the coil is used with, or firmly connected with in the sense of the present invention.

Alternatively, each coil may be arranged within the section of the instrument the coil is used with or firmly connected with in the sense of the present invention.

A coil (or several or all coils) may be built from windings.

The section of the instrument which holds sensors or coils may show a cross-section which, in at least parts of the section, is tubular (hollow). The cross-section may also show any other form, in particular, it can be solid or non-hollow.

The sensors may measure or work based on different physical measurement principles.

In certain embodiments according to the present invention electromagnetic sensors are used. This has the advantage that, for example, when compared to optical sensors, the sensors may be used within different media, housings or encapsulations without a direct visual contact being necessary.

Further, sensors that are located on the first section may differ from the sensors of the second section. A first sensor may differ from one and/or further sensors in dimension, sensitivity, measuring accuracy, the housing materials of the sensor, and other features. Also the measurement principles, in particular the physical ones, based on which the sensors work can be different. A first sensor may, for example, be based on an electromagnetic measurement principle, another sensor, for example, on an optical measurement principle.

The metrological determination of the situation of the sensors depends on the utilized measurement principles of the sensors and will not be explained in more detail here as it is well-known to the person skilled in the art.

The coordinate transformation may be determined or computed at different points in time. If for example an instrument with one or several sections comprises one or several sensors, the respective coordinate transformations can be determined at a first point in time $t_1$ and at further points in time $t_i$ (i=2, 3, 4 . . . ).

Examples for suchlike coordinate transformations which are hereafter mathematically described by homogeneous transformation matrices (T) could be:

$^{S1}T_{S2}(t_1)$ coordinate transformation from the first sensor onto the second sensor at the first point in time $t_1$; generally: the situation of the first sensor is determined or computed with reference to the second sensor at the first point in time $t_1$; or: the situation of the first sensor and the situation of the second section relative to each other is determined or arithmetically determined or computed;

$^{S2}T_{A1}(t_1)$ coordinate transformation from the second sensor onto the first section at the first point in time $t_1$;

$^{S1}T_{A1}(t_1)$ coordinate transformation from the first sensor onto the first section at the first point in time $t_1$.

The coordinate transformation from the first sensor onto the first section ($^{S1}T_{A1}$) may with a rigid first section of the instrument be considered to be approximately constant in terms of time. The same holds true for the second section and the second sensor.

The term "rigid first section" as used herein describes a non-malleable or non-deformable section or a section which, during use of the instrument, is negligibly malleable or deformable or a section which is malleable or deformable below the measuring accuracy.

The term "approximately constant in terms of time" as used herein is to be understood as constant in terms of time within measuring accuracy at two subsequent points in time (e.g., the first and second points in time $t_1$ and $t_2$ are one second or two seconds or five seconds apart):

$$^{S1}T_{A2}(t_1) \cong {}^{S1}T_{A2}(t_2).$$

According to the present invention, a criterion is used to determined whether a difference of the variable feature between a first expression at the first point in time $t_1$ and a second expression at the second point in time $t_2$ still exists or prevails at a third point in time ($t_3$).

A variable feature of the spatial reference may be present as a coordinate transformation between the first and second sensor. The expression may be determined by a first position (at the first point in time $t_1$) or a second position (at the second point in time $t_2$).

Further examples of the variable feature encompass a velocity or an acceleration of the coordinate transformation at a certain point in time or in a certain time period.

Another example of the variable feature may be the spatial situation of the first sensor and of the second sensor (situation measurement values) which are determined as coordinates in the coordinate system of the situation measurement system. These situations may also be displayed as coordinate transformation.

The degrees of freedom of a coordinate system may be considered as the basis for the coordinate transformation (as spatial reference). For example, the coordinate transformation $^{S1}T_{S2}$ at the first point in time $t_1$ has three translational and three rotational degrees of freedom in the direction of the axes of the respective coordinate system. In an x-y-z-coordinate system these translational degrees of freedom are in x-direction, y-direction and z-direction, and the rotational degrees of freedom are around the x-axis, y-axis and z-axis.

Criteria for the change of the variable feature may be, for example:
- the change of/in a degree of freedom of the coordinate transformation between the first and second sensor
- the standard deviations of a degree of freedom of the coordinate transformation between the first and second sensor across n measurement values of the sensors
- the linear assignment of a degree of freedom of the situation measurement value of the first sensor to the corresponding degree of freedom of the situation measurement value of the second sensor
- average velocity of/in a degree of freedom of the coordinate transformation between the first and the second sensor across n measurement values of the sensors
- velocities of/in a degree of freedom of the coordinate transformation between the first and the second sensor across n measurement values of the sensors
- acceleration of a degree of freedom of the coordinate transformation between the first and the second sensor across n measurement values of the sensors These criteria may be used singularly or together in arbitrary combinations.

In an embodiment according to the invention, the changes of all six degrees of freedom of the coordinate transformation between the first sensor and the second sensor too can be used together, for example, as a criterion for a change.

The term "linear assignment" as used herein is to be understood as a linear assignment (also denoted as linear assignment or linear function) of the situation measurement values of the first sensor and of the second sensor. The corresponding degrees of freedom of the measurement values of the first sensor and of the second sensor have in certain embodiments according to the present invention a linear assignment across/over at least three subsequent points in time.

In some embodiments according to the present invention the measurement data show a linear assignment only if the linear correlation is proven across at least three subsequent measurement values in all degrees of freedom of the situation measurement data. If for example all translational degrees of freedom show linear assignments but the rotational degrees of freedom (rotary movements around the coordinate axes) are sufficiently different (for example rotary movements that are opposing each other), the coordinate transformation overall does not show a linear assignment at the three subsequent points in time.

The degree of linearity can be measured by a correlation coefficient. With a correlation coefficient of one (1) or close to one (1), a high linearity is present; at zero (0) or close to zero (0), no linearity at all or only little linearity is present.

According to the invention, when determining the differences of the coordinate transformations between the single points in time, predetermined tolerance ranges can be considered in certain embodiments by the criteria.

These tolerance ranges may be determined for the linear assignment (tolerance range of the correlation coefficient "close to one" for the decision as to whether a linear assignment is present or not), for the average velocity (tolerance range of the average velocity "close to zero" for the decision "yes" or "no"), for the absolute velocities (tolerance range of the velocities "close to zero" for the decision "yes" or "no") and for the accelerations (tolerance range of the accelerations "close to zero" for the decision "yes" or "no").

Furthermore, according to the present invention, limit values for the standard deviations of the coordinate transformations can be considered when determining the differences of the coordinate transformations between the single points in time by the criteria.

In certain embodiments of the invention, a deformation of the instrument and/or interferences during metrological determination of the sensors are determined or distinguished from each other using the criterion and/or the predetermined tolerance range and/or the predetermined limit value.

According to the present invention, the method may comprise one or more of the following steps:

At each point in time, the transformation between the first and the second sensor is collected or determined. In the absence of any interference and any deformation, it is constant as compared with a set-value or setpoint, or variations are below a limit value (normal state). The set-value is being determined from the sensor values at a first point in time $t_1$ and being stored as transformation between the sensors, or it has already been stored.

If a change in the measured transformation between the sensors compared to the set-value arises, it indicates that either a deformation or an interference exists. With the deformation, the physical situation of the sensors relative to each other is permanently changed (until the next deformation) so that the set value of the transformation does not apply any more or does not hold true anymore. The deviation from the set-value is constant (after the deformation). This is detected by the described criteria.

In case of an interference, the physical situation or orientation of the sensors relative to each other still corresponds to the set-value, however an erroneous situation of at least one sensor is being detected by the interference. This results in a deviation of the transformation matrix from the set-value, the deviation existing only as long as the interference exists.

Furthermore, the deviations that are caused by an interference are not constant (also not during the interference). This is detected by the criteria described above.

With each occurrence of a deviation from the set-value, it is decided whether there is a deformation or an interference. The criteria described above serve this purpose.

In the case of a deformation, the deviation of the measured transformation between the sensors from the set-value of the transformation matrix is computed. The result is used to compute a new transformation matrix between the second sensor and the tip of the instrument. The measured transformation between the sensors is set as new set value and may be stored. Thus, the normal state is re-established until another interference or another deformation occur. The method continues in a loop corresponding to the above description.

In the case of an interference, the measurement values are processed for example by a suitable filter until the interference decays. The decay of the interference may be collected at any point in time by the monitoring of the deviation of the measured transformation between the sensors from the set-value of the transformation matrix already described. After clearance or decay of the interference, the method continues in a loop as described above.

The criteria can for example be used according to the invention as follows:

A deformation of the instrument may, for example, be determined or detected by a linear assignment between the single degrees of freedom of the measurement data of the first sensor and the second sensor across at least three subsequent measurement values after the deformation.

For example, a bending or deflection of the instrument which at a point in time $t_1$ is not yet present, can be contemplated at a point in time $t_2$. The plastic deformation is then present at a point in time $t_2$ (and lasts during the subsequent points in time). To distinguish the deformation from interferences, the situation measurement data of the first and of the second sensor may be contemplated. The situation measurement data may each be described by a transformation matrix. These transformation matrices comprise at all points in time 6 degrees of freedom each (3 translational and 3 rotational ones) which can describe the coordinate transformation from the first sensor or from the second sensor onto the coordinate system of the measurement system (or vice versa) ($T_a$ or $T_b$). If, for example, there is a linear correlation between all 6 corresponding degrees of freedom of the coordinate transformations $T_a$ and $T_b$ across, for example, three subsequent measurement values after the deformation $T_a(t_2)$ and $T_b(t_2)$, $T_a(t_3)$ and $T_b(t_3)$ and $T_a(t_4)$ and $T_b(t_4)$, a deformation of the instrument between the points in time $t_1$ and $t_2$ can be determined. The same holds true if no return from a situation that differs from the initial orientation into the initial orientation can be observed.

An erroneous position determination, caused by interferences, may, in contrast, be determined or detected if the linear assignment between at least one respective degree of freedom of the coordinate transformations $T_a$ and $T_b$ is not present across at least three subsequent points in time, e.g. $t_2$ to $t_4$, or if a return to the initial situation is detected.

In some embodiments according to the present invention, a deformation of the instrument may be determined by the average velocity of the single degrees of freedom of the coordinate transformations at at least three subsequent points in time.

A deformation of the instrument can be determined if or when the average velocity of the single degrees of freedom of the coordinate transformations of at least two subsequent measurement values is close to zero after the deformation (as an example of a criterion). A velocity close to zero indicates that the measured sensor signals at the three subsequent points in time are close to each other and thus a deformation of the instrument but not an error in the position determination can be concluded.

A failure detection can in contrast be assumed if the velocity is not close to zero. A velocity which is not close to zero may indicated that the measured sensor positions move relative to each other. This is not in line with the physical condition in which the sensors (after the deformation) should be arranged "rigid" to each other again. Thus, the measured sensor signals can be interpreted as interference signals. These are, for example, dismissed.

In the same way measured sensor signals which show the absolute velocities and occurring accelerations are used in some embodiments according to the present invention to detect deformations or errors.

The present invention relates in particular to the checking a position determination of instruments or sections hereof which warp or deform during their use, be it due to an intentional or an unintentional warp or deformation of the instrument. A warp is described here in the sense that the second section changes its situation with reference to the first section. Depending on the geometry and material characteristics of the instrument, depending on physical environmental parameters such as, for example, temperature and pressure and also depending on the forces and momenta or torques presumably applied on the instrument, it may be possible to describe the presumable warp mathematically or to approximate it with sufficient accuracy.

In a further preferred embodiment of the present invention, a tip of the instrument is the reference point for generating the position data of the second section of the instrument.

In a further preferred embodiment of the present invention, the position data measured by the sensors, or their subsequent processing in a control unit or in a computer, are output on a suitable output device. Such an output device may, for example, be a monitor.

It may be useful to not output measurement data that were determined for failure detection or that were measured as interfering signals and/or that are beyond a limit value range that was determined earlier, or to not use them in further contemplations etc. This may be realized, for example, by a threshold value filter in a corresponding computing unit.

In certain embodiments of the method according to the present invention, at least one further sensor is used on each further section, for example a third, fourth etc. sensor on each a third, fourth etc. section. With the further sensors, the spatial reference between situation or position of the sensor or of each single further sensor, on the one hand, and the first sensor and/or at least a spot on the first section, on the other hand, is determined.

Providing only one threshold value is also encompassed by the present invention.

Non-output of measurement values above or below a limit value may be advantageously suitable for improving the accuracy of the position determination of instruments and increasing the reliability with respect to the output of the actual position of the instrument. In particular, the unnoticed influence of objects in the environment of the instrument, more specific in the measurement area of the sensors on the instrument, is advantageously reduced by the described method. With respect to the described electromagnetic sensors (coil elements) this holds true for example for the influence of objects that have ferromagnetic properties. The field distortion of these objects or their influence on a position determination is decreased by the mentioned method, in particular non-rigid instruments that are suitable for intentional deformations, and for rigid but deformable instruments with situation sensors.

In yet a further preferred embodiment, the method according to the present invention is used for medical instruments. During surgical procedures in for example oral and maxillofacial surgery as well as in otorhinolaryngology, it may be very important to know the exact position of surgical instruments in order to avoid violation of vessels, nerves or other sensitive areas. At the same time, a multitude of instruments, monitoring and diagnosis devices and other aids are used during such surgeries. Quite frequently, many of these instruments and devices are made from metallic materials—for example, in order to achieve visibility on computer tomographies. Another reason for the widespread use of metallic materials in surgical instruments nowadays is the ease of sterilization, which especially in the medical field is of great importance. On the other hand, new operative operation techniques such as, for example, minimally invasive surgery is used more and more in application fields which often require exact navigation and handling of instruments in areas that are not clearly visible. Also in the application fields mentioned supra, the method according to the present invention offers major advantages compared with what is known from the state of the art.

The utilized instrument may for example be an ultrasound probe (rectal, vaginal, intravascular probe), a catheter, a suction or aspiration device, an endoscope or a pointing instrument. It may often be of advantage if at least a section comprises a geometrically defined end, so that it can, for example be usable as a pointing instrument.

By the method according to the present invention it is advantageously possible to check (or to validate) the position determination of instruments that deform during use, and/or to communicate detected artifacts or to consider them in a position determination.

The object according to the invention is also solved by the apparatus according to the preamble of claim 8. It is further accomplished by a digital storage medium according to claim 20, a computer program product according to claim 21 and a computer program according to claim 22. As the advantages that are achievable herewith completely match the advantages explained above, reference is expressly made to the above discussion to avoid repetition. The same applies to the above description of the instrument or other structural designs and features of the apparatus according to the present invention.

In certain embodiments, the apparatus according to the present invention is designed and provided and/or configured to perform the method according to the invention. In some embodiments, it comprises a correspondingly configured computing or control device. In certain embodiments, it comprises corresponding devices that are suitable and/or provided and/or configured to perform the single steps of the method according to the present invention.

In some embodiments according to the invention, the apparatus comprises at least a first section and at least a second section. The first section comprises at least a first sensor and the second section comprises at least a second sensor. At least one deformation spot is provided between the first section and the second section.

This deformation spot is, in some embodiments according to the present invention, designed as a self-retaining deformation spot, i.e. as a deformation spot (or bending spot) which is plastically malleable or which after its deforming or bending remains in the deformed or bent condition or position.

In certain embodiments according to the invention, the first section and/or the second section are provided to be variably definable or determinable.

In some embodiments according to the present invention, at least one deformation spot (e.g., a joint or a bending area) is provided between the first sensor and the second sensor.

In certain embodiments according to the invention, the deformation spot and/or the deformation area comprises an alloy.

In some embodiments according to the present invention, the alloy is or comprises a soft-annealed material.

BRIEF DESCRIPTION OF THE DRAWINGS

Hereafter, the method and the apparatus according to the present invention are exemplarily explained by the appended drawing, in which identical reference numerals denote same or identical elements. In the partially highly simplified figures.

DETAILED DESCRIPTION

Figure 1:
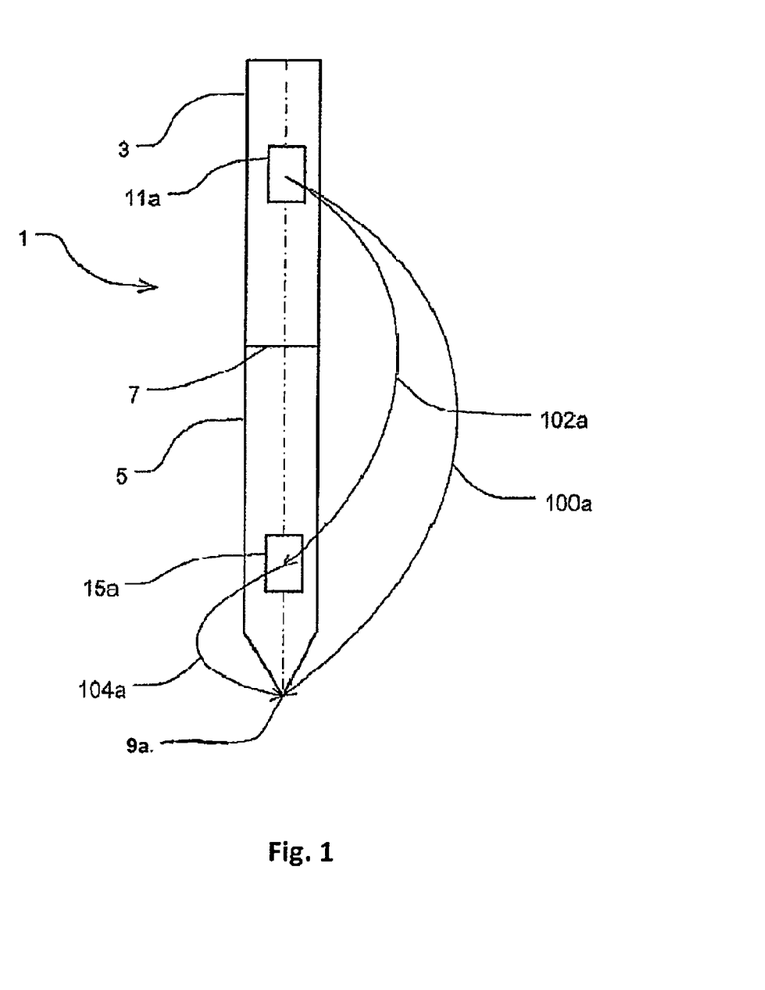
FIG. 1 shows a schematically simplified instrument of an embodiment with two sensors and two sections in the normal state, suitable to be used with the method according to the present invention.

FIG. 1 shows, schematically simplified, an instrument 1 with a first section 5 and a second section 3. Between the sections 3 and 5, the instrument comprises a parting line 7 which can be understood as a joint between the sections 3 and 5 for the intended deformation of the instrument 1 during its use. In FIG. 1, the instrument 1 is not deformed. An angulation in the area of the parting line 7 is not present. At the end of the first section 5 there is a tip 9*a* of the instrument. The first section 5 comprises a first sensor 15*a*, the second section 3 comprises a second sensor 11*a*.

A deformation of the instrument may also take place at several parting lines or without defined parting line 7. Entirely elastic or plastic distortion is also possible.

The coordinate transformation between the first sensor 15*a* and the tip 9*a* of the instrument is displayed by a transformation matrix 104*a*. A further coordinate transformation between the second sensor 11*a* and the tip 9*a* of the instrument is displayed by a transformation matrix 102*a*. By use of the coordinate transformations 104*a* and 102*a*, the situation of the tip 9*a* of the instrument is computed from the sensor values (situation data) of the first and second sensor. Hence, two measurements for the tip 9*a* of the instrument exist at one point in time. These are, as displayed in FIG. 1, (almost) identical in the non-interfered and non-deformed state.

Furthermore, a coordinate transformation between the first sensor 15*a* and a second sensor 11*a* is displayed by a transformation matrix 102*a* at the first point in time $t_1$.

The state as displayed in FIG. 1 is hereafter considered to be the normal state.

Figure 2:
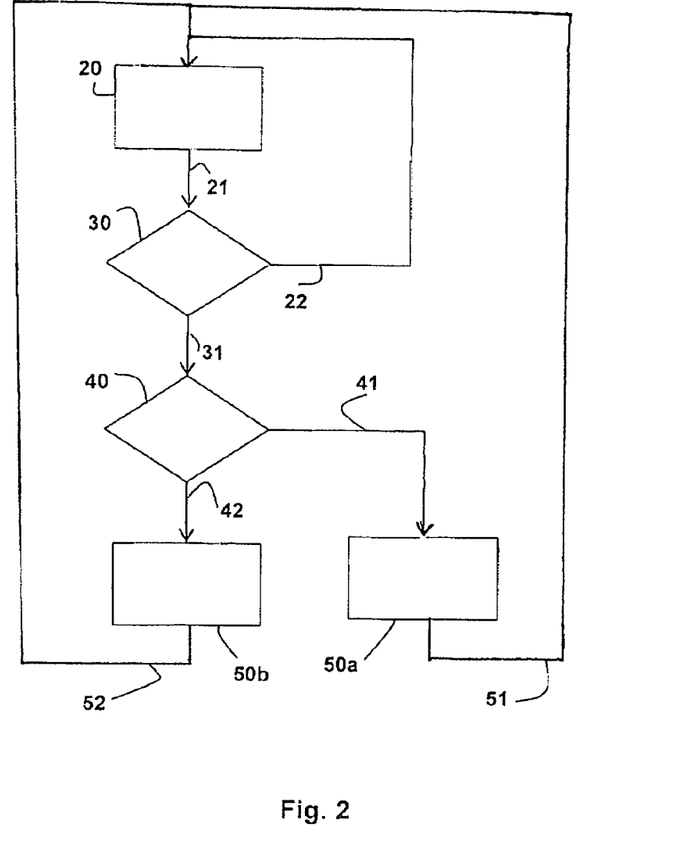
FIG. 2 schematically shows the process of the method according to the present invention.

FIG. 2 shows a flow chart of the described method. At a first point in time $t_1$, the instrument as described in FIG. 1 is present in 20 in the normal state.

At the subsequent point in time $t_2$ (21: return to 30) in 30, the transformation matrix 102a between the first sensor 15a and the second sensor 11a is contemplated. If there is no change at the point in time $t_2$ compared to the point in time $t_1$, the normal state is still present (31: return to 20).

If there is a change, a deformation or an interference is present (32).

With the method according to the invention, a check is made, in 40, as to whether at the third point in time $t_3$, the conditions as they were present at the second point in time $t_2$ are still present. This check can be made using a criterion. If the condition is not present in an unchanged way, an interference is concluded and the method is continued in 50a (41). If the condition is present in an unchanged way, a deformation is concluded and the method is continued in 50b (42).

If an interference is present, the measurement values in 50a are, for example, processed through a filter. After clearance of the interference, the normal state is present again (51: return to 20).

If a deformation is present, in 50b the new arrangement of the sensors respective to each other (caused by the deformation) is set as normal state and the new transformation from the second sensor 11a onto the tip 9a of the instrument is computed and used from this point in time as normal state (52: return to 20).

Figure 3:
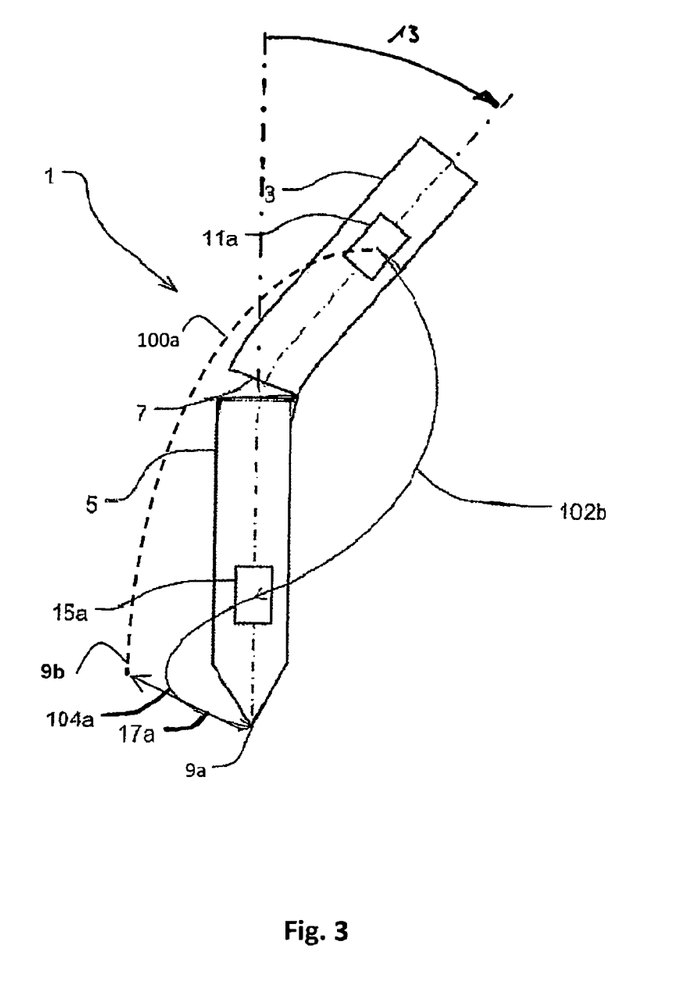
FIG. 3 shows the instrument of FIG. 1 in an intended (or intentionally) deformed state at a point in time $t_2$, at which a deformation is detected.

FIG. 3 shows the instrument 1 of FIG. 1 at a second point in time $t_2$, in a position in which the second section 3 is twisted or tilted as intended by an angle 13, when compared to the first section 5.

Thus, using the coordinate transformation 100a from the second sensor 11a, the situation of the tip 9a of the instrument is displayed incorrectly in the second sensor's 11a new situation, but in a situation 9b which is displaced by a distance 17a.

The coordinate transformation 104a from the first sensor 15a still displays the situation of the tip 9a of the instrument correctly.

Further, a coordinate transformation between the first sensor 15a and the second sensor 11a is displayed by a homogeneous transformation matrix 102b at the second point in time $t_2$. This transformation matrix 102b is unchanged compared to the transformation matrix 102a at the first point in time $t_1$.

This transformation matrix 102b is obviously based on correct measurement results as far as the second sensor 11a is concerned. In fact, the second section 3 at the second point in time $t_2$, which is shown in FIG. 2, is deformed by intended use of the instrument 1 compared to its situation in space at the first point in time $t_1$ and also compared to the first section 5.

Both the transformation matrix 102b which is changed at the second point in time $t_2$ (compared to the transformation matrix 102a at the first point in time $t_1$) and the distance 17a between the tip 9a of the instrument measured by the first sensor 15a and the spot 9b which was measured in its displaced situation by the second sensor, indicate that a deformation or an interference state are present.

In order to answer the question of whether this detected deformation is in fact present or if it is a result of errors in measurement or errors in evaluation, the method according to the present invention enables a check to be made as to whether, at a later third point in time $t_3$, the conditions are still unchanged from the conditions as they were present at the second point in time $t_2$. This check may take place using a criterion.

Figure 4:
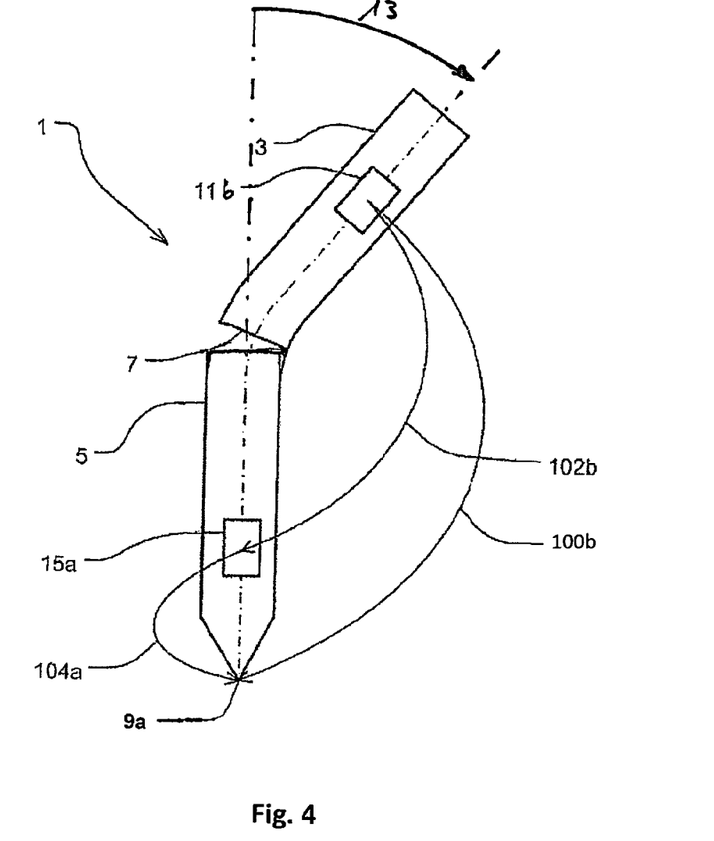
FIG. 4 shows the instrument of FIG. 1 in an intended deformed state at a point in time $t_3$, at which a deformation state was set as the normal state.

FIG. 4 shows the instrument of FIG. 3 at a third point in time $t_3$. A check was made by using the method according to the invention as to whether the condition as present at the second point in time $t_2$ is still present in an unchanged way. Thus, a factual presence of a deformation can be concluded.

The deformation state is taken from this point in time as new normal state. For this, the difference between the transformation 102a at the first point in time and the transformation 102b at the second or third point in time is computed. It is then added to the transformation 100a from the second sensor 11a onto the tip 9a of the instrument, so that the resulting new transformation 100b re-computes the situation of the tip 9a of the instrument from the sensor values of the second sensor 11a in a correct way.

Figure 5:
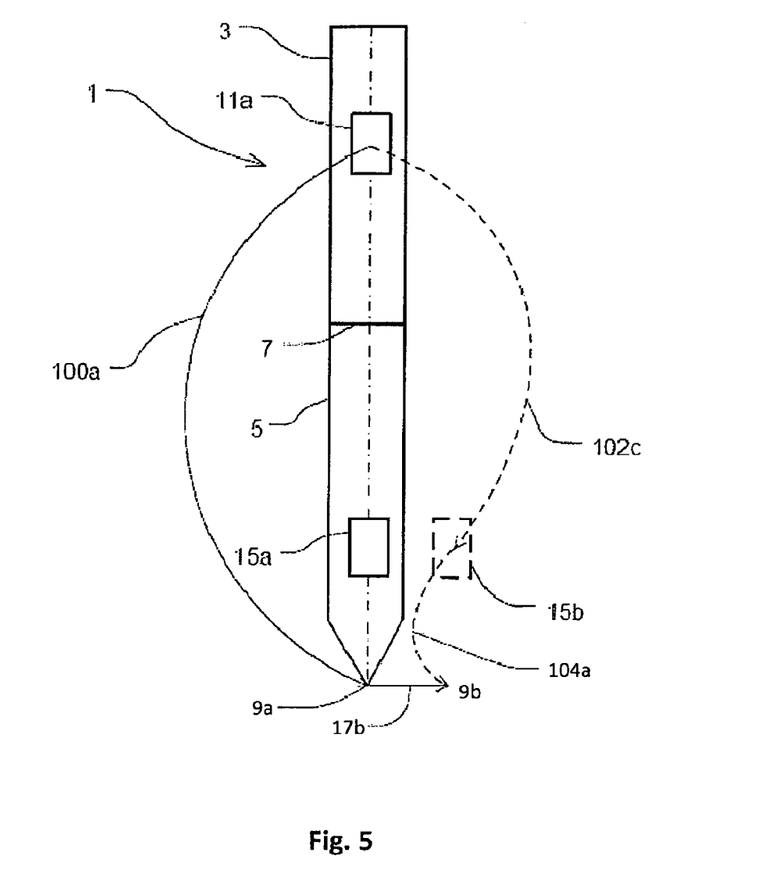
FIG. 5 shows the instrument of FIG. 1 with indicated interfered measurement of the position of the first sensor.

FIG. 5 shows the instrument of FIG. 1. The coordinate transformation between the second sensor 11a and the tip 9a of the instrument is displayed by the transformation matrix 100a.

However, a displaced position 15b of the first sensor, caused by an interference during measurement of the first sensor 15a, is measured. Thus, by also using the coordinate transformation 104a the position of the tip 9a of the instrument is measured displaced by a distance 17b (the section 1 is considered to be rigid).

Thus, the coordinate transformation between the second sensor 11a and the new, erroneously measured position 15b of the first sensor is displayed by the homogeneous transformation matrix 102c.

The coordinate transformation 100a between the second sensor 11a and the tip 9a of the instrument remains unchanged. Thereby, it is assumed that the interference of the measurement of the first sensor 15a with the result of the new, measured position 15b does not have any effect on the measurement of the sensor 11a.

The erroneous nature of the determined position 15b of the first sensor may occur by a control of the position of the first sensor of the first section 3 at the third point in time $t_3$, as described above.

Figure 6:
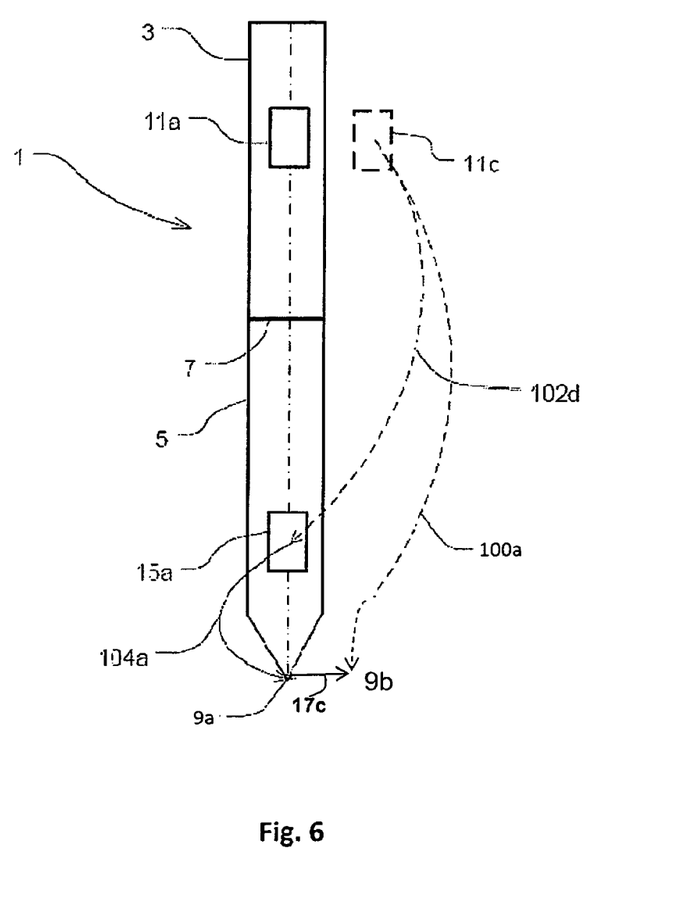
FIG. 6 shows the instrument of FIG. 1 with indicated interfered measurement of the position of the second sensor.

FIG. 6 shows, in a simplified way, the instrument 1 of FIG. 1 in its non-deformed state of FIG. 3.

Compared to FIG. 5 the measurement of the second sensor 11a is now interfered. It is thus measured as erroneous position 11c.

Thus, through the coordinate transformation 100a from the second sensor 11a, now measured as position 11c, the tip of the instrument 9a is not measured any more, but instead a tip of the instrument 9b which is displaced by a distance 17c.

Also, the coordinate transformation between the second sensor, measured as position 11c, and the first sensor 15a is displayed by the new homogeneous transformation matrix 102d.

The coordinate transformation 104a between the first sensor 15a and the tip 9 of the instrument remains unchanged. Thereby, it is assumed that the interference of the measurement of sensor 11a (with the result of the erroneously assumed position 11c) does not have any effect on the measurement of the sensor 15a.

Also in the instrument of FIG. 6, a detection as to whether the measured position change represents an artifact or is an actual position change can be made by controlling whether the changed position of the first sensor or of the second sensor still exists at a third point in time $t_3$, as described with regard to FIGS. 3 to 5.

What is claimed is:

1. A method for checking a situation or a position of an instrument having at least a first section and at least a second section, wherein the first section comprises at least a first sensor and the second section comprises at least a second sensor, and wherein the method comprises a metrological determination of the situation or the position, or its change, of the first sensor and the second sensor, the method comprising the steps of:

determining an expression of a variable feature of a spatial reference between the situation or the position of the first sensor and/or at least one spot on the first section, on the one hand, and the situation or the position of the second sensor and/or at least one spot on the second section or the first section which is referenced by the second sensor, on the other hand, at at least a first point in time, a second point in time, and a third point in time; and     determining by a criterion whether a difference in the expression of the variable feature between a first expression at the first point in time and a second expression at the second point in time still exists at the third point in time.

2. The method according to claim 1, wherein, on the basis of the determining by the criterion, a distinction is made between whether the difference in the expression of the variable feature between the first expression at the first point in time and the second expression at the second point in time is based on a deformation of the instrument or on a different influence of the spatial reference.

3. The method according to claim 1, wherein at least one further sensor is used each on a further section, wherein the spatial reference between the situation or the position of each further sensor, on the one hand, and the first sensor and/or the at least one spot on the first section, on the other hand, is determined.

4. The method according to claim 1, wherein a change of the spatial reference is determined when determining the position using the criterion and complying with a predetermined tolerance range and/or a predetermined limit value.

5. The method according to claim 1, wherein if a change of the spatial reference is permanent the expression of the variable feature of the spatial reference at the third point in time is set as a new initial expression of the method.

6. The method according to claim 1, wherein a tip of the instrument is the at least one spot on the first section.

7. The method according to claim 1, wherein the instrument is a medical instrument.

8. An apparatus for performing the method according to claim 1.

9. The apparatus according to claim 8, the apparatus comprising at least a first section and at least a second section, wherein the first section comprises at least a first sensor, wherein the second section comprises at least a second sensor, and wherein between the first section and the second section, a deformation spot is provided.

10. The apparatus according to claim 9, wherein at least one of the at least one first sensor and the at least one second sensor comprises at least one coil.

11. The apparatus according to claim 10, wherein the at least one coil has at least one continuous or reach-through interior.

12. The apparatus according to claim 10, wherein the at least one coil is wound around a section of the instrument or within the section.

13. The apparatus according to claim 12, wherein the section of the instrument has a hollow tubular cross-section.

14. The apparatus according to claim 12, wherein the section of the instrument has a non-hollow cross-section.

15. The apparatus according to claim 9, wherein the first section and/or the second section are provided to be variably definable.

16. The apparatus according to claim 9, wherein between a first sensor and a second sensor, the deformation spot is provided.

17. The apparatus according to claim 9, wherein the deformation spot and/or a deformation area comprises an alloy.

18. The apparatus according to claim 17, wherein the alloy is a soft-annealed material.

19. The apparatus according to claim 8, wherein the apparatus comprises a medical instrument.

20. A digital storage medium, in particular a disk, CD or DVD, with electronically readable control signals that may interact with a programmable computer system such that the steps of a method according to claim 1 may be prompted.

21. A tangible computer program product with a program code comprising instructions for prompting the steps of the method according to claim 1 when the tangible computer program product runs on a computer.

22. A computer program product with a program code comprising instructions for prompting the steps of the method according to claim 1 when the computer program product runs on a computer.

* * * * *